United States Patent
Perez et al.

(10) Patent No.: US 9,421,539 B2
(45) Date of Patent: Aug. 23, 2016

(54) ABSORBENT/SOLUBILIZING MATERIALS BASED ON MICROPOROUS ORGANOGELS

(71) Applicant: CENTRE NATIONAL DE LA RECHERCHE SCIENTIFIQUE (CNRS), Paris (FR)

(72) Inventors: Emile Perez, Colomiers (FR); Sophie Franceschi-Messant, Pechbusque (FR); Isabelle Rico-Lattes, Auzielle (FR); Jean-Christophe Garrigues, Toulouse (FR)

(73) Assignee: CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 14/388,910

(22) PCT Filed: Apr. 2, 2013

(86) PCT No.: PCT/EP2013/056930
§ 371 (c)(1),
(2) Date: Sep. 29, 2014

(87) PCT Pub. No.: WO2013/144370
PCT Pub. Date: Oct. 3, 2013

(65) Prior Publication Data
US 2015/0059441 A1    Mar. 5, 2015

Related U.S. Application Data

(60) Provisional application No. 61/667,642, filed on Jul. 3, 2012.

(30) Foreign Application Priority Data

Mar. 30, 2012    (FR) ...................... 12 52902

(51) Int. Cl.
| | |
|---|---|
| *G01N 30/00* | (2006.01) |
| *G01N 33/18* | (2006.01) |
| *B01D 53/14* | (2006.01) |
| *B01J 20/291* | (2006.01) |
| *B01L 3/00* | (2006.01) |
| *B01D 53/02* | (2006.01) |
| *C02F 1/28* | (2006.01) |
| *C09K 3/32* | (2006.01) |
| *G01N 1/22* | (2006.01) |
| *B01D 15/08* | (2006.01) |
| *G01N 1/10* | (2006.01) |
| *G01N 30/06* | (2006.01) |
| *B01J 20/26* | (2006.01) |
| *B01J 20/285* | (2006.01) |
| *B01J 20/30* | (2006.01) |
| *B01J 20/28* | (2006.01) |
| *C02F 101/32* | (2006.01) |
| *C02F 103/00* | (2006.01) |
| *C02F 1/40* | (2006.01) |

(52) U.S. Cl.
CPC ............... *B01L 3/5023* (2013.01); *B01D 15/08* (2013.01); *B01D 53/02* (2013.01); *B01D 53/025* (2013.01); *B01J 20/268* (2013.01); *B01J 20/285* (2013.01); *B01J 20/28047* (2013.01); *B01J 20/291* (2013.01); *B01J 20/3064* (2013.01); *B01L 3/502707* (2013.01); *C02F 1/285* (2013.01); *C09K 3/32* (2013.01); *G01N 1/10* (2013.01); *G01N 1/2214* (2013.01); *G01N 30/06* (2013.01); *B01D 2253/20* (2013.01); *B01D 2253/202* (2013.01); *B01D 2253/308* (2013.01); *B01D 2253/311* (2013.01); *B01D 2257/708* (2013.01); *B01D 2257/93* (2013.01); *B01J 2220/82* (2013.01); *C02F 1/40* (2013.01); *C02F 2101/32* (2013.01); *C02F 2103/007* (2013.01); *C02F 2305/14* (2013.01)

(58) Field of Classification Search
CPC ............... B01D 2253/20; B01D 15/08; B01D 2253/202; B01D 2253/308; B01D 2253/311; B01D 2257/60; B01D 2257/708; B01D 2258/06; B01D 2257/93; B01D 53/025; B01J 20/291; C02F 1/825
See application file for complete search history.

(56) References Cited

U.S. PATENT DOCUMENTS

| | | | | |
|---|---|---|---|---|
| 6,080,281 | A * | 6/2000 | Attia | ......................... 204/157.3 |
| 2003/0022389 | A1 * | 1/2003 | Miller et al. | ................... 436/174 |
| 2011/0124790 | A1 * | 5/2011 | Penicaud | ...................... 524/424 |

FOREIGN PATENT DOCUMENTS

| | | |
|---|---|---|
| CN | 102139203 A | 8/2011 |
| EP | 1566213 A1 | 8/2005 |

(Continued)

OTHER PUBLICATIONS

Lukyanova et al., "Soft Microporous Green Materials from Natural Soybean Oil", May 14, 2008, CHEMSUSCHEM, Vol. 1, Issue 6, pp. 514-518.*

(Continued)

*Primary Examiner* — Paul Hyun
(74) *Attorney, Agent, or Firm* — Birch, Stewart, Kolasch & Birch, LLP

(57) ABSTRACT

The present invention relates to the use of a microporous organogel for the capture of fluids by adsorption and/or for the controlled release of fluids after solubilization. The fluids are, in particular, air or water pollutants or volatile substances. The invention also relates to the use of a microporous organogel in a process for analyzing the captured fluids. The invention also relates to any fluid sensor by molding of a microporous organa gel.

2 Claims, 3 Drawing Sheets

(56) References Cited

FOREIGN PATENT DOCUMENTS

| | | |
|---|---|---|
| FR | 2886867 A1 | 12/2006 |
| JP | 2012046596 A | 3/2012 |

OTHER PUBLICATIONS

International Search Report received in corresponding PCT/EP2013/056930, mailed May 24, 2013.

Maity et al., "Fabrication of nanoporous material from a hydrophobic peptide", CrysteEngComm, The Royal Society of Chemistry, 2011, 13, 3064, pp. 3064-3071.

Venditti, et al. "Removal of chromate from water by a new Ctab-silica gelatin composite", ScienceDirect, Elsevier, Journal of Colloid and Interface Science, 310, 2007, pp. 353-361.

Venditti, et al., "Effects of sulfate ions and slightly acidic pH conditions on Cr(VI) adsorption onto silica gelatin composite", Elsevier, Journal of Hazardous Materials 173, 2010, pp. 552-557.

\* cited by examiner

ABSORBENT/SOLUBILIZING MATERIALS BASED ON MICROPOROUS ORGANOGELS

CROSS REFERENCE TO RELATED APPLICATIONS

This application is a §371 National Stage Application of PCT/EP2013/056930, filed Apr. 2, 2013, which claims the benefit of U.S. Provisional Application No. 61/667,642, filed Jul. 3, 2012, which claims priority to FR 1252902, filed Mar. 30, 2012.

BACKGROUND

1. Field of the Invention

The present invention relates to the novel use of microporous organogels as adsorbents and solubilizing agents in the field concerning the trapping of fluids.

2. Description of Related Art

Before they can be analyzed, fluids which by definition group together gases or liquids must be trapped. The fields of application are varied and diverse, and mention may be made for example of the analysis of polluting agents or fragrances whether or not in the form of volatile compounds.

Nevertheless, the adsorbent materials used at present are very rapidly saturated on the surface which prevents the trapping of fluids in large amounts.

In addition, the porous adsorbents currently available are of mineral origin (activated charcoal, zeolite, clays) or synthetic polymers.

The trapped products are difficult to recover and the density, porosity and polarity of these materials cannot be adjusted.

These materials are also difficult to regenerate leading to high costs of use.

Additionally, there is a true need at the current time to develop new materials in the field of fluid trapping.

SUMMARY

In surprising manner, the Applicant has evidenced the use of microporous organogels in the area of fluid adsorption, which can be efficiently applied to the trapping of fluids since they are capable of solubilizing the adsorbed fluids.

A porous material is defined as a material that allows a fluid, such as a liquid or gas, to flow through the pores or interstices of the material. Porosity is an essential characteristic for the use of the organogels according to the present invention by contributing to the adsorption and solubilization of fluids.

All gels, however, are not porous materials and thus cannot give rise to the phenomenon of porous adsorption and solubilization, unlike the porous organogels according to the present invention.

These microporous organogels thus constitute a novel family of materials having the twofold property of adsorption and solubilization which makes these materials unique in the field of adsorption.

Organogels are semi-solid materials consisting of an organic liquid or oil immobilized by a three-dimensional network of fibers resulting from the self-assembly of a polymer organogelator or low molecular weight organogelator, preferably a low molecular weight organogelator.

The gels according to the present invention have in addition the advantage of passing reversibly from a solid state to a liquid state.

A low molecular weight organogelator corresponds to a small organic molecule capable of gelling in small proportions a broad range of organic liquids. By low molecular weight is meant a molecular weight of less than 1000 g/mol, and more particularly less than 500 g/mol.

It is to be noted that the proportion of organogelator controls the heat resistance of the organogel but also its mechanical strength. This parameter therefore allows easy adapting of the material in relation to use-related constraints.

Also, the polarity of the organogel depends on the organic liquid or oil to be gelled. The lipophilicity parameter is the parameter that controls the kinetics of fluid trapping and/or release and can be adjusted in the case of organogels by choosing suitable organic liquids or oils to be gelled according to their log P value.

On this account, the use of a vegetable oil of strong hydrophobic nature will allow a hydrophobic organogel to be obtained.

Microporous organogels are used in cosmetics, pharmaceuticals and foodstuffs and have the advantage of being able to contain ingredients or active principles to facilitate the adding and the stability of said ingredients or active ingredients to compositions.

More particularly, microporous organogels can be used in tissue engineering to prepare artificial extracellular matrices as described in the thesis by Lukyanova, 22 Jan. 2009: "Preparation de matrices microporeuses d'organogels et evaluation en culture cellulaire" and in the article by Lukyanova et al.: "Colloids and Surfaces B"; Biointerfaces, 2010, 79, 105-112.

These microporous organogels are obtained via the method described in the thesis by Lukyanova and in the article by Lukyanova et al.: "Soft Microporous Green Materials from Natural Soybean Oil"; ChemSusChem, 2008, 1, 514-518.

For the preparation of these organogels, one particularly suited organogelator is 12-hydroxystearic acid (HSA) derived from castor oil. More particularly, 12-hydroxystearic acid is able to form organogels with organic aliphatic, alicyclic or aromatic liquids. It is also able to form organogels with vegetable oils such as sunflower oil and soybean oil.

A method using the aqueous dissolution of a template of solid water-soluble particles of calibrated size allows controlled microporosity to be obtained inside the organogels. These water-soluble solid particles are more commonly called porogens.

To obtain a microporous organogel, a first step consists of preparing templates of water-soluble porogens, in particular sugars such as sucrose for example or icing sugar, or salts such as sodium chloride for example, by agglomeration with a minimum amount of water. The paste obtained is then pressed in a mold and dried to obtain compact templates of porogens.

In a second step, these compact templates of porogens are immersed in the molten organogel in liquid form.

After impregnation, the mixture is cooled and the templates impregnated with organogel are immersed in distilled water at room temperature until complete dissolution of the porogens particles, thereby forming pores inside the organogel.

Table 1 below groups together data corresponding to pore size distribution and effective porosity in relation to the type of porogen, type of oil and to the initial water content of the template.

TABLE 1

Composition and characteristics of matrices containing capric/caprylic triglycerides and soybean oil.

| Organogel | Porogen agent | Initial water content, wt. % | Pore size distribution (mean) [a], µm | Effective porosity [b], % |
|---|---|---|---|---|
| Capric/caprylic triglycerides (15 wt. % HSA) [c] | Sugar | 3.5 | 25-400 (220) | 65.2 ± 1.5 |
| | | 2 | 25-500 (290) | 64.3 ± 0.4 |
| | Salt (NaCl) | 3.5 | 25-500 (230) | 61.9 ± 1.6 |
| | | 2 | 25-500 (230) | 59.9 ± 1.3 |
| | Salt (NaCl) | 3.5 | 25-300 (150) | 60.2 ± 1.0 |
| | | 2 | 25-350 (150) | 61.7 ± 1.5 |
| | Icing sugar | 3.5 | 10-75 (30) | 66.3 ± 1.7 |
| | | 2 | 10-60 (40) | 59.7 ± 1.1 |
| Soybean oil (7.5% wt. % HSA) [c] | Sugar | 3.5 | 25-400 (220) | 64.5 ± 1.2 |
| | | 2 | 25-500 (270) | 60.9 ± 0.8 |
| | Salt (NaCl) | 3.5 | 25-500 (230) | 61.1 ± 1.9 |
| | | 2 | 25-550 (230) | 55.7 ± 2.1 |
| | Icing sugar [d] | 3.5 | 10-70 (30) | 64.1 ± 0.9 |
| | | 2 | 10-60 (40) | 57.9 ± 1.3 |

[a] Determined by image analysis;
[b] measured by liquid displacement;
[c] matrices with 30% HSA for the capric/caprylic triglycerides and 15% HSA for soybean oil give identical results;
[d] soybean oil organogel containing icing sugar with 15 wt. % HSA.

These novel microporous organogels, such as characterized in Table 1, have shown good biodegradability. In addition, the mechanical strength of these porous matrices is fully adapted for the reconstruction of soft tissue. In vitro biological tests on these microporous organogels have allowed the evaluation of their capacity as artificial extracellular matrix for the culture of fibroblasts. It has also been evidenced that these matrices prove to be capable of maintaining the survival and proliferation of cells over a long period of 21 days. To conclude, the potential of these novel microporous organogels as artificial extracellular matrices has been evidenced for tissue engineering. Nothing has thus prejudged the use of these microporous organogels in the field concerning the trapping of fluids.

The subject of the present invention is therefore the use of a microporous organogel for trapping fluids by adsorption and/or for the controlled release of fluids after solubilization.

Advantageously, the fluids are concentrated in the microporous organogel.

DETAILED DESCRIPTION OF A PREFERRED EMBODIMENT

According to one particular aspect of the invention, the fluids contain organic compounds.

By concentration of a fluid in the microporous organogel is meant an increase in the quantity of fluid matter within the microporous organogel leading to a reduction in the equivalent quantity of fluid matter in the outside medium (water or air). Concentration is therefore taken in the meaning of the partition ratio of a fluid between water or air and the microporous organogel.

Adsorption is based on the property of solid or gelled surfaces to fix molecules of gas or liquids reversibly via weak Van der Walls-type bonds. The fluids adsorbed on the surface are solubilized in the organogel on account of its gelled liquid nature.

By controlled release is meant the isolating of the adsorbed fluid after solubilization of the microporous organogel. The mechanism of controlled release is based on the oil/water or oil/air partition ratio of the fluid but also on the fibrous network of the microporous organogel whose density and meshing limit free diffusion.

By organic compound is meant a molecule comprising at least one carbon atom.

According to one particular aspect of the invention, the fluids contain air or water polluting agents, in particular hydrocarbons and/or heavy metals.

Polluting agents in the meaning of the present invention are molecules which, beyond a certain threshold, develop negative impacts on an ecosystem or an environment in general. Typically, the polluting agents may be hydrocarbons, i.e. organic compounds exclusively containing atoms of carbon and hydrogen. The polluting agents may also be heavy metals described as such on account of their high density. Mention may be made for example of lead, cadmium, mercury, arsenic, chromium, nickel, copper, zinc.

Thus, in a particularly advantageous field of application of the invention, the microporous organogel is used to trap polluting agents.

Indeed, numerous human and industrial activities are the source of organic and hydrophobic pollutants such as pesticides, herbicides, or hydrocarbons and motor vehicle oils (lubricants, brake fluid, hydraulic fluids). Some surface pollution is very visible, in particular that caused by detergents which foam on the surface of water, or oil spills which are veritable ecological catastrophes.

However, there exists a surface pollution that is underestimated, whose composition is poorly identified, and that is hence much more insidious.

These latter types of pollutants are often less dense than water and therefore form surface pollution. Hydrophobic pollutants may also exist in emulsified form obtained after shearing by wind or rain. This emulsified form is metastable and after creaming will produce a surface film.

Indeed, hydrophobic surface films may prove to be highly polluting. The thin interface layer lying between water and air, called neuston, forms the communication gateway between these two environments and its deterioration may have serious consequences on exchanges between the two. This interface may accumulate hydrophobic pollutants on the surface, these pollutants having a greater or lesser physical and chemical barrier effect.

Neuston corresponds to the surface of oceanic and inland waters and covers more than 70% of the world surface area, its biodiversity including several thousand species. Pollution which accumulates thereupon may therefore have serious consequences for its inhabitant organisms. In addition, the mix of all these pollutants, spread out and concentrated in a thin layer, is exposed to intense radiation which may lead to other even more harmful pollutants.

In addition, surface pollutants are mostly non-volatile residues of hydrocarbons (gasoline, diesel oil) or motor vehicle oils (engine lubricants, brake fluid, hydraulic fluids). The accumulation of these pollutants in rainwater from road networks, airports or port installations raises concerns as to the possible repercussions on public health and the biodiversity of aquatic environments.

Also, the characterization and quantification of these hydrophobic surface pollutants is not easy. Indeed, these pollutants remain very difficult to capture. This difficulty is related to the fact that these pollutants extend over very large surface areas, often in very thin films, and conventional water sampling methods only allow an infinitely small proportion thereof to be harvested which often does not lend itself to detection. Therefore, although the presence of these surface pollutants has been proven, their extent and composition are not precisely known nor are all the impacts they may have on the environment.

Within this context, the microporous organogel used in the present invention is particularly suited on account of its low density, which in particular is lower than that of water thereby leading to its buoyancy. The microporous organogel is therefore able to absorb and solubilize in large quantity various types of hydrophobic pollutants present in water, whether emulsified or in thin surface films.

According to another aspect of the invention, the fluids are volatile substances, particularly gases or vapors, and preferably pheromones of insects, aromas of plants, flowers or resins.

The ability of fats and oils to adsorb scents has been ascertained since antiquity. This method allowed the use of plant aromas for hundreds of years. This method, known as cold enfleurage, was reserved for fragile flowers and is described in particular in the article by Lawrence et al.: Progress in essential oils, Perfumer & Flavorist 1994, 19(5), 83. The principle is based on the greater solubility of odoriferous molecules in oil than in plant products, with the natural transfer of scents from the plant to the fat or oil.

The microporous organogel of the invention is therefore particularly advantageous in that it forms a microporous fat having a very high specific surface area promoting adsorption.

Typically, the microporous organogel used in the context of the present invention is hydrophobic. By hydrophobic is meant the fact that the gelled liquid is non-polar or weakly polar, and that it cannot establish bonds or interactions with water.

Particularly, the microporous organogel used in the context of the present invention has a porosity of between 10% and 90%, preferably between 55% and 70%.

The percentage porosity of the microporous organogel is obtained and calculated using the following method:
The water-saturated microporous organogel is weighed and a weight W1 is obtained.
The microporous organogel is then dehydrated by lyophilization and is again weighed to obtain a weight W2.
The weight of trapped water W0 is equal to W1−W2.
The volume occupied by the water V1 is equal to W0/d1 (d1=density of water).
The volume occupied by the organogel is equal to W2/d2 (d2=density of the organogel).
The percentage porosity is equal to $(V1/(V1+V2))\times100$.

More particularly, the mean diameter of the pores of the microporous organogel used in the context of the present invention is between 0.5 μm and 550 μm, advantageously between 1 μm and 550 μm, more advantageously between 10 μm and 550 μm, even more advantageously between 50 μm and 450 μm, preferably between 100 μm and 300 μm, and particularly advantageously the mean diameter of the pores of the microporous organogel is about 220 μm.

The invention also concerns the use of a microporous organogel such as defined above, obtained using a method comprising a step to prepare the organogel and a step to form pores in said organogel, in particular by aqueous dissolution of a template of solid water-soluble particles of calibrated size, previously impregnated with organogel, preferably of sugars, advantageously sucrose, or of salts, advantageously sodium chloride.

Advantageously, the microporous organogel is prepared from an organogelator, in particular 12-hydroxystearic acid, and from an organic liquid non-miscible in water, in particular an oil, preferably soybean oil.

The invention also concerns the use of a microporous organogel such as defined above in a method for analyzing trapped fluids, in particular by liquid or gas chromatography and/or by mass spectrometry and/or as substrate for solid-phase extraction (SPE).

Advantageously, the analysis of the trapped fluids is performed by simple dissolution of the organogel used in the context of the present invention in a suitable solvent.

As suitable solvent, mention may be made of organic solvents, in particular tetrahydrofuran.

The invention also concerns any fluid trap which has been shaped to a suitable form by molding a microporous organogel such as defined above.

By suitable shape is meant a geometric shape of the trap that is adapted to the trapping area and trapping medium of the fluids. For example, a disc or plate shape is well adapted for trapping fluids on the surface of water but much less so for trapping at depth. In this case a sphere or cylinder shape is preferred.

Therefore, the use of a microporous organogel such as defined above for trapping fluids has numerous advantages.

Indeed, its unique twofold property of adsorption and solubilization allows the trapping and accumulating of large quantities of fluids. The technique for preparing the microporous organogel is clean and low-cost and provides for controlled porosity by adjusting pore volume and pore size. This preparation technique also allows the density and polarity of the microporous organogel to be adjusted in relation to the type of gelled liquids and their mixture and in relation to the choice of organogelator.

The ingredients used to obtain the microporous organogel are derived from renewable resources and the preparation method pays heed to the environment.

Microporous organogels also allow direct analysis of the trapped fluids by simple dissolution in a suitable solvent.

The following examples are used to illustrate but in no way limit the invention.

EXAMPLE A

Demonstration of the trapping of a hydrocarbon film on the surface of water.

Hydrocarbon model: Dodecane stained with vermilion red (5% v/v)

Trap: Pellet of microporous organogel (soybean oil, HSA organogelator (15% by weight), sugar template).

Pellet characteristics: Dehydrated pellet, diameter=30 mm, thickness=5 mm, mean porosity 67%, mean pore diameter 220 μm.

Trapping Protocol and Kinetics Monitoring:
A film of stained dodecane 1 mm thick is formed on a water surface. On this film a pellet is deposited whose staining is filmed over time. Image analysis software allows monitoring of the adsorption kinetics by photodensitometry.

Figure 1:
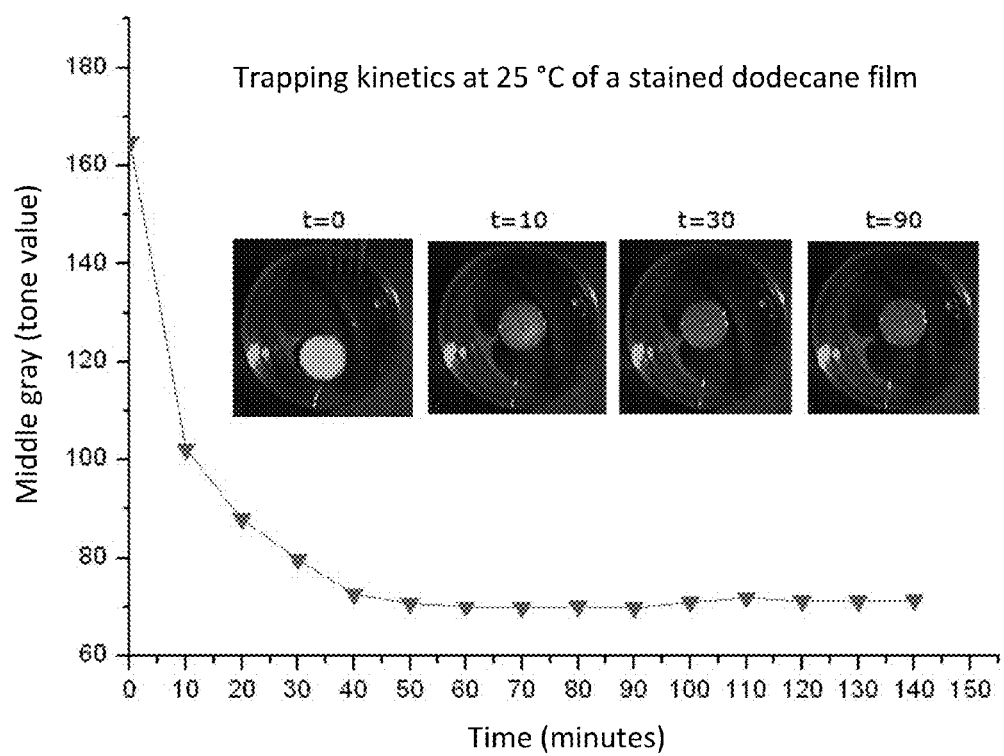
FIG. 1 shows a curve of the trapping kinetics at 25° C. of a stained dodecane film.

Results:
The kinetics curve (FIG. 1) shows rapid adsorption of the dodecane film with a plateau after 60 min.

Remark: A non-dehydrated pellet has the same adsorption capacities with slightly slower kinetics (plateau after 75 min).

EXAMPLE B

Field demonstration of the trapping of surface pollutants

Test site: Lac du Perget (Colomiers, France, 31770)

Trap: Pellet of microporous organogel (soybean oil, HSA organogelator (15% by weight), sugar template).

Pellet characteristics: Dehydrated pellet, diameter=30 mm, thickness=5 mm, mean porosity 67%, mean pore diameter 220 µm.

Trapping Protocol:

The pellet is deposited on the surface of the water inside a floating hoop (30 cm in diameter) to delimit a trapping surface. The pellet is recovered after 2 hours.

Controls: Non-trapping pellet.

GC Analysis:

HPLC-UV analyses performed on an Alliance 2695 system, with PDA 996, on an Xbridge Shield RP18 column, 2.1×100 mm, 3.5 µm. Gradient T0: 100% $H_2O$, T60 min: 100% ACN, flow rate 0.3 ml/min. UV analysis at 230 nm. Solubilization of the pellet in 1 ml THF, injection 10 µl.

Figure 2:
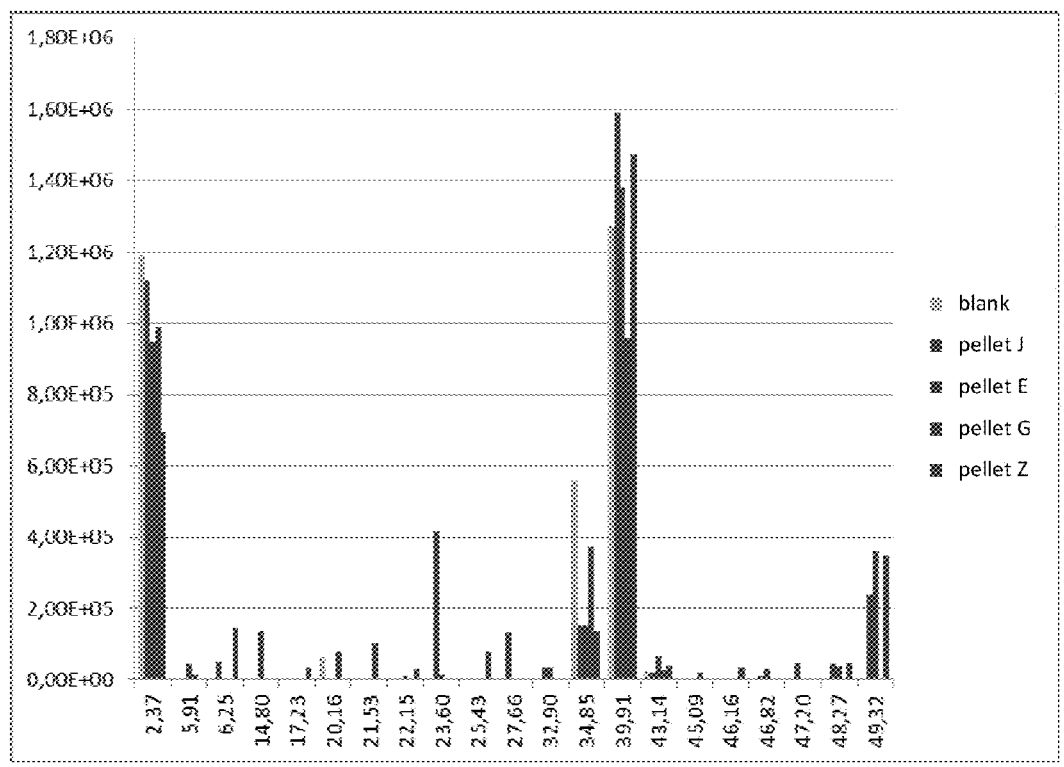
FIG. 2 is a chromatogram of lavender aromas trapped by the microporous organogel used according to the invention.

Results:

FIG. 2 shows that in the different pellets analyzed (pellets J, E, G and Z), between 2 and 8 peaks characteristic of surface pollution were identified, since they were not found in the analysis of the control pellet (blank).

EXAMPLE C

Demonstration of Scent Trapping

Plant tested: True lavender (*Lavandula angustifolia*), fresh flowers and essential oil.

Trap: Pellet of microporous organogel (soybean oil, HSA organogelator (15% by weight), sugar template).

Pellet characteristics: Dehydrated pellet, diameter=30 mm, thickness=5 mm, mean porosity 67%, mean pore diameter 220 µm.

Trapping Protocol:

Pellet suspended above the flowers in a hermetically sealed bowl, for 1 hour at 25° C.

Controls: Non-trapping pellet and direct injection of essential oil.

GC Analysis:

After trapping, the pellets were dissolved in 1 ml of THF and analyzed by gas-phase chromatography coupled with detection by mass spectrometry.

Figure 3:
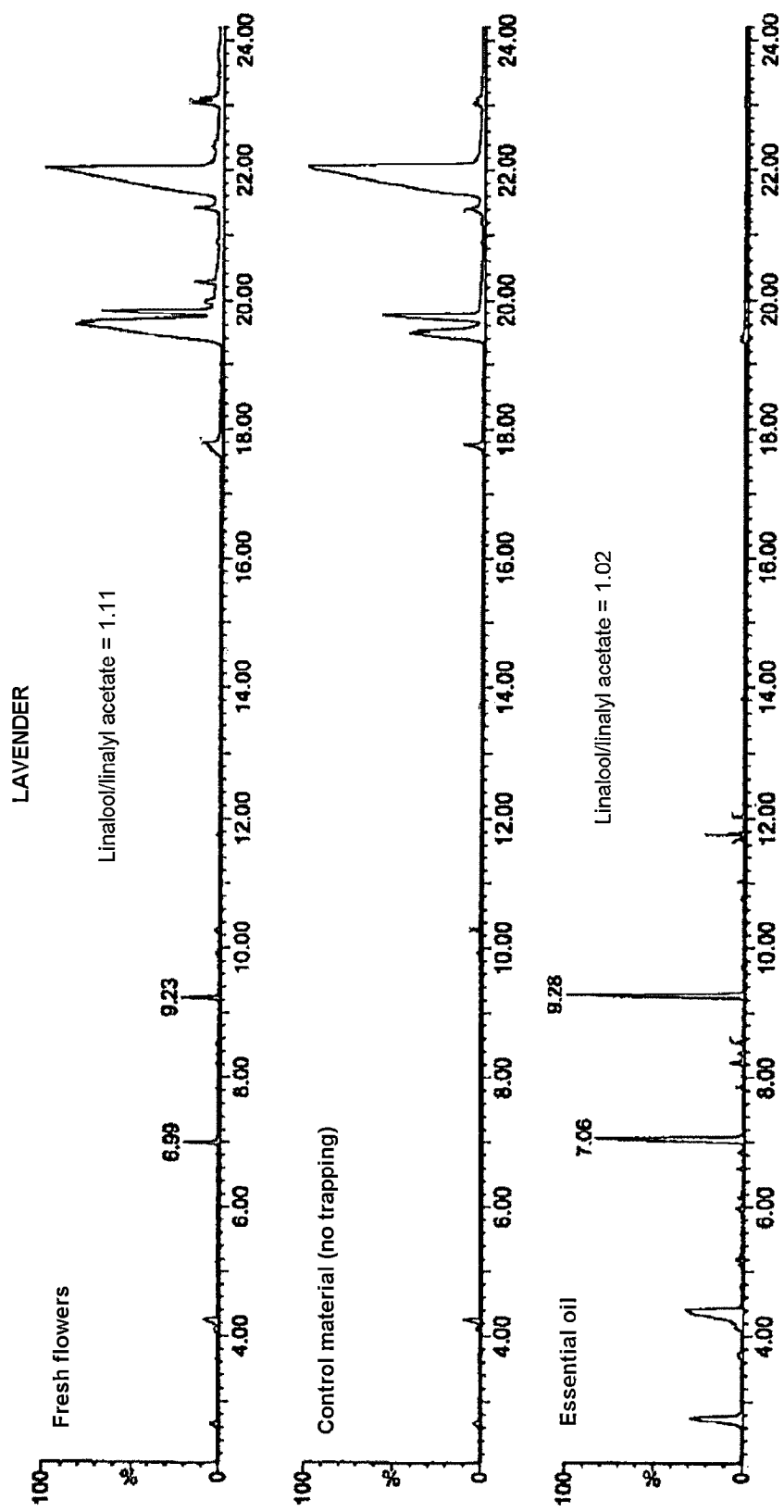
FIG. 3 is a chromatogram of fluids trapped by different pellets of microporous organogel used according to the invention.

Results:

The chromatogram shown in FIG. 3 corresponds to three analyses: essential oil injected directly, a control pellet and trapping on fresh flowers.

The peaks at 7.0 and 9.2 minutes respectively correspond to linalool (L) and linalyl acetate (LA), the two main odorant molecules of lavender. Their presence confirms the adsorbing efficacy of the material on volatile compounds. The ratios of these two peaks (L/LA) are equivalent in the essential oil and in the trapping on fresh flowers, which indicates that after adsorption in the material the olfactory signature is maintained.

EXAMPLE D

Preparation of the Microporous Organogel

1. Preparation of the Organogel

Fixed concentrations of gels are obtained by adding weighed quantities of 12-hydroxystearic acid to soybean oil and the mixture is heated to 70° C. (>T° gelling). The solution is cooled to room temperature and a gel is obtained. The gel state is confirmed using the upturned bottle test.

2. Formation of the Pores

Templates of particles of agglomerated porogens (sucrose, sodium chloride) are prepared by mixing porogen particles with 2% or 3.5% by weight of distilled water. The paste mixture is manually pressed in a Teflon® mold and dried for 30 to 35 minutes at 80° C. The templates of agglomerated porogen particles are then immersed in the molten organogel at a temperature of 70° C. (>T° gelling), and left for 12 to 15 minutes for good impregnation of the templates. After cooling to room temperature, the impregnated and gelled models are immersed at room temperature in distilled water renewed every day for 7 days to dissolve the porogen particles and then air dried.

The invention claimed is:

1. A method for analyzing trapped fluids, which comprises
    absorbing and solubilizing a fluid in a microporous organogel,
    dissolving said organogel by simple dissolution with a solvent, and
    analyzing the trapped fluids,
    wherein said oranogel is a semi-solid material comprising an oil immobilized by a three-dimensional network of fibers obtained by self-assembling in an organogelator.

2. The method according to claim 1, wherein the analyzing is carried out by liquid or gas chromatography, and/or by mass spectrometry, and/or as substrate for solid-phase extraction (SPE).

* * * * *